United States Patent [19]

Tseung et al.

[11] Patent Number: 5,439,649

[45] Date of Patent: Aug. 8, 1995

[54] AUTOMATED STAINING APPARATUS

[75] Inventors: Ken Tseung; Wai Bun Wong, both of Fremont; Glenn K. Takayama, Danville; Christopher M. Jones, Walnut Creek; Krishan L. Kalra, Danville, all of Calif.

[73] Assignee: BioGenex Laboratories, San Ramon, Calif.

[21] Appl. No.: 129,243

[22] Filed: Sep. 29, 1993

[51] Int. Cl.[6] ............................................. B01L 11/00
[52] U.S. Cl. ....................... 422/99; 73/864.01; 118/300; 422/63; 422/67; 422/100
[58] Field of Search ................ 422/63, 65, 67, 99, 422/100; 436/63, 46, 54, 174, 180; 427/4; 118/58, 59, 300; 73/864.01

[56] References Cited

U.S. PATENT DOCUMENTS

| | | | |
|---|---|---|---|
| 3,853,092 | 12/1974 | Amos et al. | 118/56 |
| 4,004,550 | 1/1977 | White et al. | 118/314 |
| 4,013,038 | 3/1977 | Rogers et al. | 118/5 |
| 4,034,700 | 7/1977 | Basset et al. | 118/2 |
| 4,043,292 | 8/1971 | Rogers et al. | 118/5 |
| 4,088,797 | 5/1978 | Johnson | 427/2 |
| 4,200,056 | 4/1980 | Johnson | 118/401 |
| 4,985,206 | 1/1991 | Bowman et al. | 422/99 |
| 5,009,185 | 4/1991 | Stokes et al. | 118/52 |
| 5,180,606 | 1/1993 | Stokes et al. | 427/2 |
| 5,231,029 | 7/1993 | Wootton et al. | 435/289 |

OTHER PUBLICATIONS

"Ventana 320 Automated Immunostaining System," marketing brochure for Ventana Medical System, Inc., Tucson, Ariz. (date unknown).
"Jung Histostainer Ig Automated Immunostainer," marketing brochure for Leica Instruments GmbH, (date unknown).

*Primary Examiner*—James C. Housel
*Assistant Examiner*—Jan M. Ludlow
*Attorney, Agent, or Firm*—Richard Neeley; Luann Cserr

[57] ABSTRACT

An automated microscope-slide-staining apparatus, having a supporting framework; an arm moveable in three dimensions attached to the framework; apparatus for moving the arm; a hollow tip head located on the arm; apparatus for alternatively supplying positive or negative gas pressure to the hollow tip head; a removable wash/blow tip having an exit slit, the wash/blow tip being adapted to be removably attached to the hollow tip head by a preselected movement of the arm; a wash/blow tip holder at a first fixed location on the framework; a reagent application tip holder at a second fixed location on the framework for holding a reagent application tip, the reagent application tip being adapted to be removably attached to the hollow tip head by a preselected movement of the arm; a reagent container holder at a third fixed location on the framework; a microscope slide holder at a fourth fixed location on the framework, the microscope slide holder being adapted to removably contain the microscope slide; and control apparatus for controlling movement of the arm between the locations, whereby the tip head picks up the wash/blow tip or the reagent application tip in response to movement of the arm under control of the control apparatus and moves to one or more of the locations to pick up a reagent in the reagent container or dispense the reagent on the slide or to dispense a gas through the wash/blow tip over the slide. Components of the apparatus and methods of staining are also part of the invention.

24 Claims, 12 Drawing Sheets

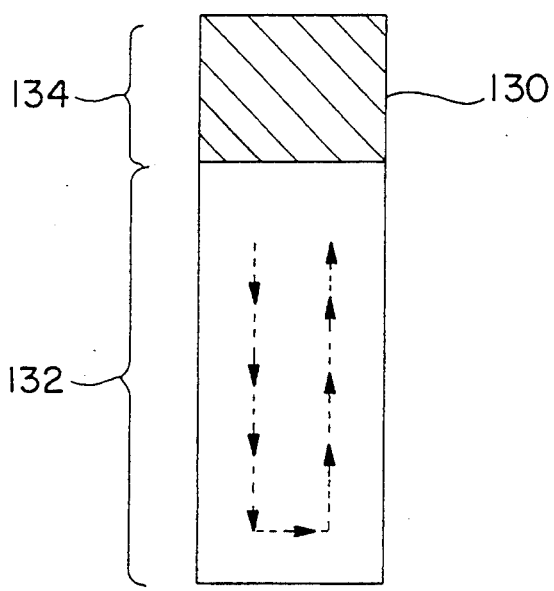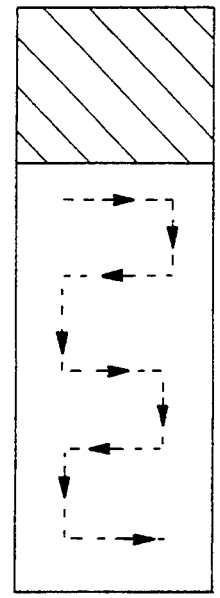
FIG. 7A  FIG. 7B
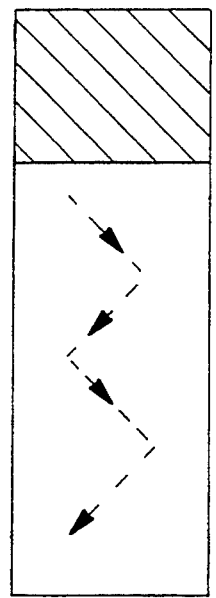
FIG. 7C

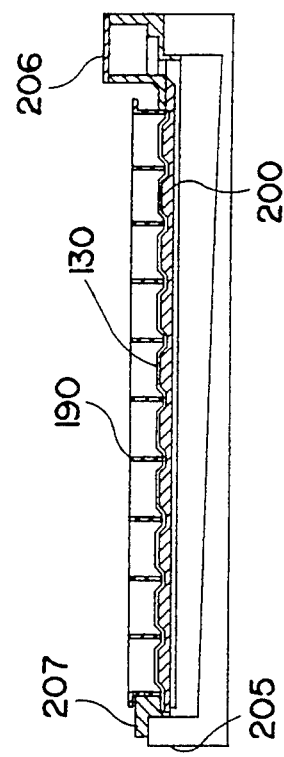
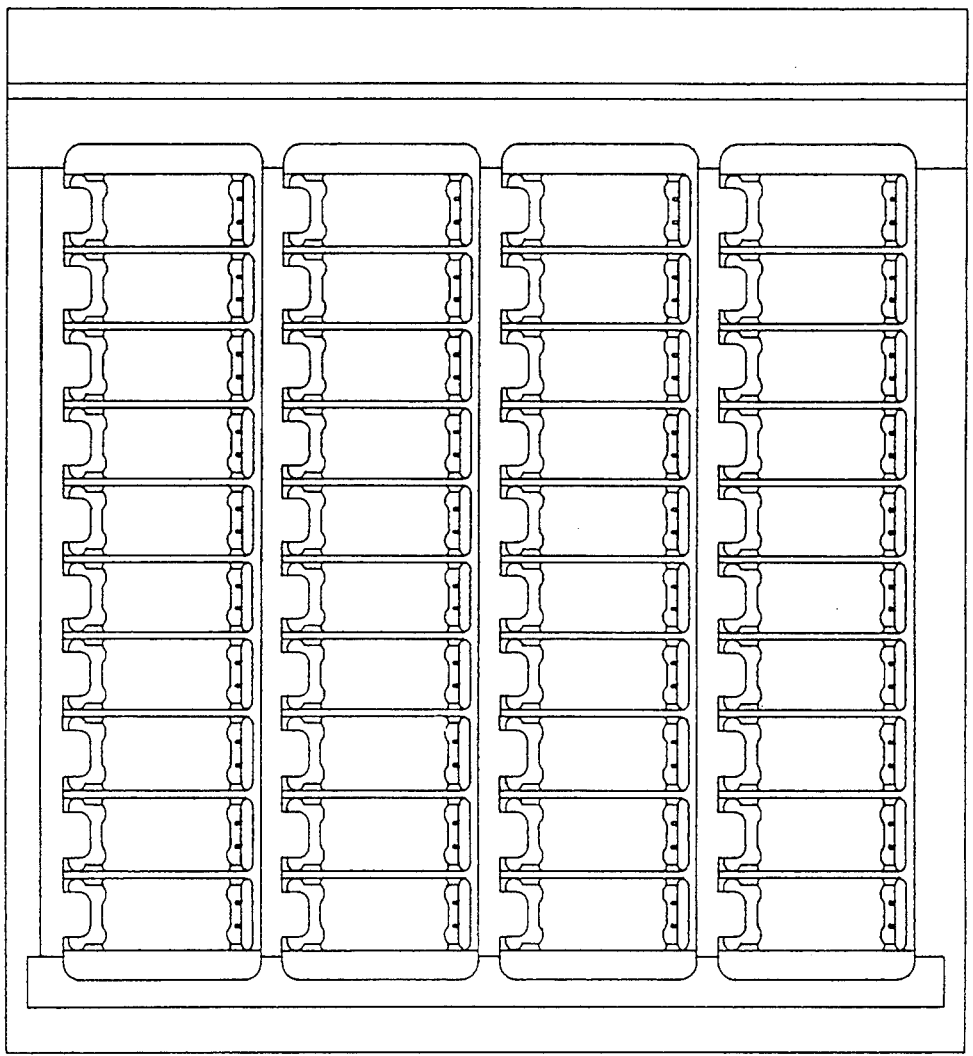
FIG. 11B
FIG. 11A 5,439,649

AUTOMATED STAINING APPARATUS

TECHNICAL FIELD

This invention relates to automated equipment used in the staining of tissues and cells on microscope slides.

BACKGROUND

Microscopic examination of unstained cell and tissue preparations often suffers from a lack of contrast between individual cells and the background matrix or between individual parts of cells. In order to alleviate this difficulty, dyes (stains) that are taken up differentially by cells or parts of cells have been used in microscopic examination of tissues for over a century.

Because of the manner in which slides with tissue preparations are prepared (see Elias, J., "Immunohistopathology: A practical Approach to Diagnosis" ASCO Press, 1990, pp. 3-4, for examples of such preparation), the size and/or location of a tissue sample on a microscope slide can vary considerably within a relatively large area of the slide. In order to apply a stain to the correct location on a slide and to provide rinsing and other manipulation steps at appropriate times and in fight amounts, until recently all such staining operations were carried out by hand. It is apparent, however, that modem laboratories that examine large numbers of tissue preparations find it desirable to automate the staining process. Accordingly, a number of manufacturers have developed equipment for automated staining of tissue preparations on microscope slides.

For example, U.S. Pat. No. 4,985,206 describes an apparatus and process for automating the application of staining reagents to a thin tissue section mounted on a microscope slide. The apparatus and method use a channel-defining element that is assembled with the microscope slide to provide an enclosure of capillary dimensions into which liquids can be injected. Liquids are added sequentially to the capillary space, where the addition of a new liquid forces out the previous liquid. A plurality of these assemblies of microscope slides and specialized covers can be placed in a rack on an apparatus for automated addition of liquids.

A further automated immuno staining apparatus referred to as the Ventana 320 TM is produced by Ventana Medical Systems, Inc. of Tucson, Ariz. This apparatus applies a liquid known as Liquid Coverslip TM to each slide prior to reagent addition. Liquid Coverslip TM is a non-aqueous material having a density less than that of water. When a reagent dissolved in water is added to a microscope slide, the reagent sinks to be bottom of the Liquid Coverslip TM for spreading across the surface of the slide. Slides are organized on a carousel which rotates beneath a dispensing head for application of reagents or wash fluids.

Leica produces an automated staining apparatus known as the Jung Histostainer Ig TM. This is another carousel-type device, but reagents are applied by a spraying operation rather than by dropping liquid onto an organic film. The apparatus contains a permanent reagent spraying head that can be moved along a single axis to provide spray coverage over a microscope slide located on the rotating tray when the slide is rotated into a position underneath the head. Excess reagent is removed by a permanent clearing nozzle which blows air in a pressure front across the slide, forcing excess liquid off at the completion of the reagent incubation step.

All of these apparatuses have attempted to solve certain conflicting goals in automated apparatuses of this type. For example, it is desirable to use a minimum of expensive or toxic reagents, particularly reagents used in immuno staining (e.g., antibodies and other reagents of biological origin), while insuring that complete coverage of the microscope slide by the reagent will occur. However, the last-referenced spraying operation above uses an excess of reagent which must be removed in order to obtain satisfactory coverage. The other techniques require additional manipulative steps, such as the use of a hand-assembled cover or an additional liquid reagent to provide for proper spreading of the reagent. It would be desirable to have an automated apparatus that can use regular microscope slides without additional manipulation and that does not require the use of either excess reagent or the use of an organic liquid with additional manipulation and disposal steps.

Accordingly, further developments that allow individual slides to be treated differently in a single batch operation and that provide an automated procedure that uses reagents efficiently remain needed.

SUMMARY OF THE INVENTION

It is an object of the invention to provide an automated staining apparatus that is readily programmable to allow automated staining of individual microscope slides with different techniques without operator intervention in a single operation.

It is a further object of this invention to provide an automated staining apparatus that uses staining reagents efficiently with a minimum of waste and without extraneous steps.

These and other objects of the invention have been attained by providing an automated staining apparatus, comprising a supporting framework; an arm moveable in three dimensions attached to the framework; means for moving the arm; a hollow tip head located on the arm; means for alternatively supplying positive or negative gas pressure to the hollow tip head; a removable wash/blow tip having an exit slit substantially equal in length to the width of a microscope slide, the wash/blow tip being adapted to be removably attached to the hollow tip head by a preselected movement of the arm; a wash/blow tip holder at a first fixed location on the framework; a reagent application tip holder at a second fixed location on the framework for holding a reagent application tip, the reagent application tip being adapted to be removably attached to the hollow tip head by a preselected movement of the arm; a reagent container holder at a third fixed location on the framework; a microscope slide holder at a fourth fixed location on the framework, the microscope slide holder being adapted to removably contain the microscope slide; and control means for controlling movement of the arm between the locations, whereby the tip head picks up the wash/blow tip or the reagent application tip in response to movement of the arm under control of the control means and moves to one or more of the locations to pick up a reagent in the reagent container or dispense the reagent on the slide or to dispense a gas or liquid through the wash/blow tip over the slide.

The invention also provides various subcomponents of the apparatus that are specifically adapted to the staining of tissue on slides with this apparatus. A key component is a wash/blow head which comprises a hollow body member having an internal cavity; a linear exit slit providing fluid communication between the internal cavity and the external environment surrounding the tip, the linear exit slit being substantially identical in length to the width of a microscope slide with which the tip is to be used; and means for removably attaching the hollow body member to a hollow tip head in the apparatus of the invention and providing access to the internal cavity for gas or liquid supplied through the tip head.

In addition, the apparatus carries out a technique for applying stain to tissue preparations on unknown (to an instrument) locations on individual slides that is not specific to the apparatus of the invention but which can be adapted to other automated equipment or to hand operations. This method comprises applying a thin fill of water to a horizontal upper surface of a microscope slide and applying a water soluble staining reagent to the film of water in a pattern insufficient to fully cover the slide when the slide is dry, whereby the reagent diffuses through the film to reach substantially all of the surface on which a tissue may reside while using only a minimum volume of reagent.

Other aspects of the invention will be apparent from the following more detailed description.

BRIEF DESCRIPTION OF THE DRAWINGS

The invention will be better understood by reference to the following detailed description of specific embodiments when considered in combination with the drawings that form a part of this specification, wherein:

FIG. 7: Plan view of microscope slides showing exemplary reagent dispensing patterns for the method of the invention for applying stain to slides.

FIG. 11: Two views of a drain pan/heating block assembly for use in the embodiment shown in FIGS. 1–3.

DESCRIPTION OF SPECIFIC EMBODIMENTS

Figure 1:
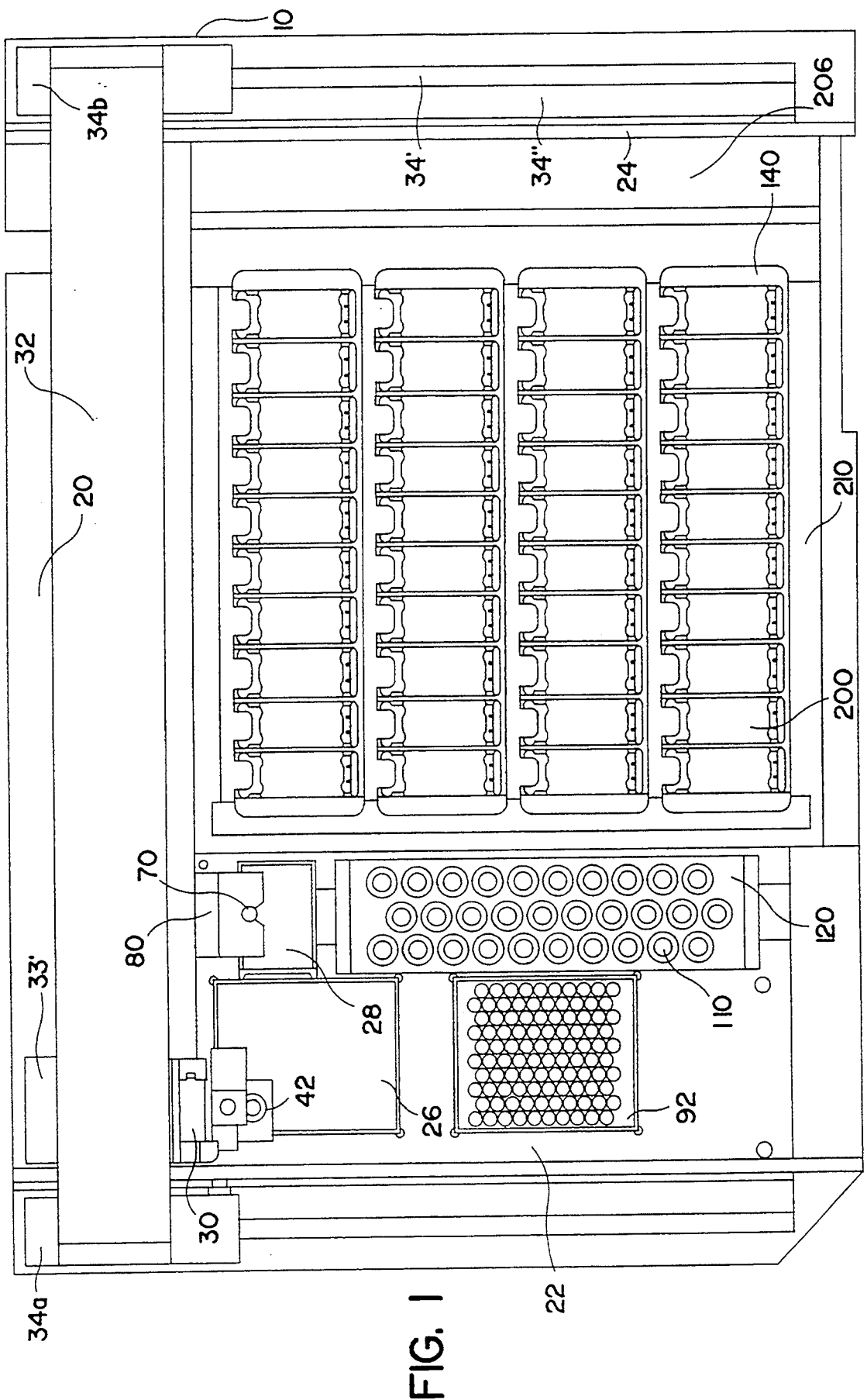
FIG. 1: Plan view of a first embodiment of an apparatus of the invention (shown without a top cover on the apparatus).

The present invention provides an automated apparatus for staining tissue preparations on microscope slides as well as various subsystems used in this apparatus and a method of staining that is adapted for automated staining operations and can be used with a variety of apparatuses.: The apparatus will first be described generally along with its operation, after which the apparatus and various component parts will be described in detail with reference to the figures that form part of this specification.

The apparatus of the invention comprises a supporting framework to which an arm movable in three dimensions is attached. Motors or other means for moving the arm are provided under the control of a computer or other electronic control device that allows programming of movement of the arm between various work locations on or within the framework. A hollow tip head is located on the arm so that liquids or air can be dispensed or withdrawn through the tip head to provide for the various work operations described below. In some embodiments of the invention, the arm is configured so as to have either multiple, permanently attached tips with different functions or multiple disposable tips located on the arm at the same time. However, in preferred embodiments of the invention a single, hollow tip head is provided to which individual tips having different functions will be attached. In a most preferred embodiment, the tip head is adapted to pick up disposable plastic pipette tips from the standard containers in which such tips are supplied (for example, Catalog No. 3510-R from E&K Scientific Products, Saratoga, Calif.). These disposable pipet tips are currently sold in a container which presents the base of the tip for insertion of a hand-held pipette by a pressing motion of the end of the pipette body into the hollow tip, the tips being arranged in an array so that all individual tips in the container are accessible to the operator. As will be apparent from the description below, the same standard box of pipet tips can be used in the apparatus of the present invention.

A key element of the apparatus of the invention is a removable wash/blow tip having an exit slit that is usually equal or substantially equal in length to the width of a microscope slide. If the slit is not equal to the width of a microscope slide with which it is intended to be used, it is preferred that the slit be slightly wider than the microscope slide. A narrower slit is less efficient in removing liquid from the microscope slide surface as described below. However, the practical width of a slit is limited by the desire to have a number of microscope slides closely arranged together in the apparatus of the invention and further to avoid wasting buffer or other wash solutions that are applied to a slide through the tip. In the blowing operation that removes excess wash/buffer solution, the exit slit on the wash/blow tip provides a "wall" of air that pushes excess liquid from the surface of a microscope slide as the tip is passed over and parallel to a microscope slide (described later in detail). This wash/blow tip is adapted to be removably attached to the same hollow tip head to which the disposable pipet tips are attached. Both of these attachment (and optionally detachment) operations can be carded out by a preselected movement of the arm, much in a same manner that disposable pipet tips are now pressed onto and later removed from the end of a handoperated pipet.

The framework of the apparatus is provided with holders at fixed locations on the framework for both the wash/blow tip and the reagent tips, among other removable items. Thus, programming of the arm to move to a particular fixed location and carry out a preselected motion or other operation discussed herein allows the individual tips to be placed onto or released from the hollow tip head. A holder for a reagent container (the reagent container being for stain or various solutions associated with staining) and a microscope slide holder are also present on a framework at other fixed locations. Thus, standardized motions of the arm can be programmed into the control unit so that individual microscope slides at specific fixed locations in the microscope slide holder can be treated with reagents and/or wash fluids obtained from reagent containers or from liquids supplied through the hollow tip head on the movable arm.

In a typical operation of the apparatus of the invention, multiple slides, each generally having a tissue sample at some location on its upper surface, are placed horizontally in a tray that is inserted into the apparatus at a fixed location, usually at a location having registration pins that fit into registration holes in the tray (or similar registration means) so that the individual microscope slides are always located in the same relative positions on the frame of the apparatus. The apparatus is programmed as appropriate for the individual slides being treated and reagents, and reagent containers are placed at their own predetermined locations in the apparatus in the same manner as the tray described above. Likewise, reagent application tips are also made available for pickup by the moveable arm. For example, a standard box of 1-ml pipet tips can be placed at its predesignated location in the apparatus.

Once all components are in place, the apparatus carries out all reagent application, incubation, heating (if necessary or appropriate), and sample rinsing steps to perform the desired staining operation. In a typical operating sequence, the movable arm picks up a detachable wash/blow tip having a slit exit, and a buffer solution is applied to each of the sample slides being treated in a particular cycle by a liquid supply line and wash buffer reservoir attached via the supply line to the hollow tip head. The apparatus then uses the same wash/blow tip to blow excess buffer off the slide prior to reagent delivery. This is accomplished by blowing air through the tip while the head travels down the length of the slide; a "wall" of air exits the slit and removes excess buffer from the slide without disrupting the tissue sample. A small amount of buffer is left on the slide to assist in reagent spreading. The wash/blow tip is then returned to its holder by the automated arm.

The arm then picks up a disposable pipet tip from the pipet tip box that has been inserted into the reagent application tip holder in the apparatus. The arm with the pipet tip attached picks up a reagent to be applied to a slide or to a group of slides from a reagent vial. A number of slides can be treated with reagent at the same time. The reagent is dispensed on the slide in a preassigned pattern that works in combination with the thin liquid film on the microscope slide to assure spreading of the reagent over the entire surface of the slide to which the tissue may be attached. The thin liquid film allows less reagent to be used than would be required if the film were not present to assist reagent spreading.

The disposable pipet tip is then discarded, and the movable arm picks up the wash/blow tip for adding buffer to and then blowing excess buffer off the next group of slides to be processed while the rest group of slides are being incubated with the reagent, after which the wash/blow tip is returned to its holder. The arm then picks up the next available disposable tip from the tip box, and reagent is drawn into the tip and applied as before. Appropriate steps are repeated until all slides have been treated with reagent or until a reagent incubation is complete so that reagents must be removed from appropriate slides.

Once a reagent incubation is complete, slides are rinsed when the movable arm picks up the wash/blow tip again and buffer is applied to the slide to rinse off the majority of the reagent. The wash/blow head then blows the excess buffer from the slide, and the slide is rinsed a second time with the on-line buffer, if necessary. This procedure of rinsing and drying a slide is repeated as necessary depending upon the individual stain and the appropriate procedure for rinsing the reagent. The control mechanism, generally a programmable computer, keeps track of the time of the various incubation and repeats the steps above as appropriate in order to apply reagent to all of the slides that have been inserted into the tray.

A special feature of the apparatus of the invention that allows efficient use of reagents is the method of spreading reagents described above and further described in detail below. When a standard aqueous staining reagent is dropped onto a glass slide, the reagent tends to stay in the location where dropped rather than spreading over the entire surface area of the slide. Since the location of the tissue preparation on a slide is variable and may not be located in the same place from one slide to the next, automated procedures previously had to apply the reagent over the entire area of the slide. While this could be accomplished by applying a relatively large amount of a dilute reagent, not all staining operations allow the use of dilute reagents, and some stains are sufficiently expensive so that applying concentrated reagent over the entire slide, including areas where no tissue is present, would be a major cost of operation. Accordingly, a special application system has been devised for use in the apparatus of the present invention; this system can be used generally in the manner described here for other automated equipment.

The slide to which stain will be added is first washed with an aqueous wash solution, usually a buffer, that contains one or more surfactants which reduce the surface tension of water. However, it is not satisfactory merely to flood a slide with an aqueous solution of surfactant, since a concentrated reagent added to the slide will merely be diluted on the slide. Accordingly, the wash/blow tip of the invention is designed so that excess buffer can be blown off the washed slides to produce a thin film of the aqueous solution. The height of the wash/blow tip slit exit above the microscope slide, the pressure of the compressed air being blown through the tip, and the rate of movement of the tip are selected to leave a controlled amount of buffer on the slide. If too much buffer is left, the reagents will be diluted as discussed above and will not work correctly. If too little buffer is left, the buffer will evaporate prior to reagent application, and the reagents will not spread. Specific techniques for controlling the wash/blow tip to select the amount of buffer are described below.

In addition to the buffer and use of the wash/blow tip as described above, the method of the invention also provides dispensing of reagents on the slide in a pattern that assists spreading. A pattern is selected so that reagent is not required to diffuse for great distances through the surface film; for example, convoluted application pattern can be selected so that reagent need not diffuse more than one-fourth (or some other fraction) of the width of the microscope slide. The combination of the buffer film and the application pattern (usually dropwise or in a stream) ensures adequate coverage of the slide regardless of the location of the tissue and allows less reagent to be used than would be required in the absence of a surface film. In a typical operation, the amount of reagent added is less than that which would be required to cover the slide if no aqueous film were present on the slide.

In addition to these general operations and components of the invention, the apparatus of the invention can contain additional subsystems for convenience, such as drain pans, heating blocks, and other components that are described below in more detail.

The invention now being generally described, the same will be described in reference to the figures using the same reference numbers throughout to represent either identical parts that appear in different views of the same embodiment or parts in different embodiments that have identical functions.

FIG. 1 shows a first embodiment of the invention in a plan view from above. In order to make visible the movable arm and other working parts of the apparatus, FIG. 1 is illustrated without the normal cover that would normally form the upper surface of the apparatus and act with remaining walls to enclose the working parts and microscope slides. In this view, the font of apparatus 10 is at the bottom of the figure.

In this view, movable arm 30 is visible in the upper-left (back-left when viewed horizontally) corner of the interior of Frame work 20 the forms the cabinet surrounding the working parts of apparatus 10. Frame 20 is formed from various components such as baseplate 22 and side plate 24 that form the cabinet. The various locations (and the corresponding parts of the apparatus or materials that are inserted into the apparatus at these locations) are visible on base plate 22. Movable arm 30 will carry out the operations of the apparatus is visible in its home position in the back-left comer of the apparatus (upper-left portion of the FIG. 1 ). Slightly in front of and to the fight of the arm home position is a drain bin 26, which is simply a container into which pipet tips 90 (described later) are discarded. Drain bin 26 can be provided with a drain line to a waste container and in any event is removable from its standard location for disposal of tips (and optional draining of collected fluid). This and other parts of the apparatus are adapted to be retained in a specific location on baseplate 22 by providing matching projections and depressions or other means for locating the indicated part of the apparatus on the base plate at a fixed location.

Immediately in front of drain bin 26 in this first embodiment is the fixed location of a reagent application tip holder 100 (not visible in this view). In this first embodiment holder 100 is adapted to retain in position a standard pipe pit tip box 92 containing an array of disposable pipet tips 90. An example of an appropriate holder 100 or pipet tips 90 (actually for tip box 92) is a raised area on baseplate 22 around which the base of pipet box 92 snugly fits.

To the fight of pipet tip box 92 is a reagent container holder 120, in this embodiment in the form of a reagent rack. The reagent rack 120 can either be affixed to the baseplate 22, or in the manner described above it can be adapted to be removable from the baseplate for loading with reagent containers 110 in a more convenient location. The reagent rock is adapted be to retained by the baseplate in a fixed location and orientation, so that any given reagent container will always be in the same relative position on baseplate 22.

Immediately behind reagent rack 120 is wash/blow tip 70 and its holder 80. Below holder 80 is a drip pan 28, which can be connected to an external drain or merely made removable for disposal of wash liquids that may drip off of tip 70 when it is present its holder 80.

To the fight of wash/blow tip holder 80 and reagent rack 120 are four 10-well microscope slide trays 140. Each troy 140 is retained in a fixed location and orientation relative to baseplate 22 and the remainder of the frame so that each microscope slide retained in a well is in a fixed location relative to the baseplate 22. Visible through the open bottom surfaces of the wells of trays 140 are heating blocks 200 and drain pan 210; these components are described in more detail in later figures.

Movable arm 30 is moved to different locations over baseplate 22 by the action of various motors that operate in combination with sliding tracks to precisely position arm 30 at its desired location within Frame 20 in order to carry out the operations that are described here. Visible in FIG. 1 at the top at the top of the figure is the X-axis track 32, in this embodiment the X-axis being the principal longer horizontal axis of the apparatus. In the embodiment shown a single X-axis track 32 is supported at either end on bearing shafts and brackets 34a (the left bracket) and 34b (the right bracket and shaft). The Y-axis is the principle shorter horizontal axis of the embodiment as shown. A step motor is used in these embodiments under the control of the computer or other control apparatus (described later). Part of one motor mount 33' for X-axis motor 33 is visible in this figure. Bearing shafts 34' and shaft supports 34' are also visible as part of the Y-axis track. The Z-axis in this embodiment is the orthogonal vertical axis and is perpendicular to the plane of FIG. 1.

In a preferred working embodiment, flexible electronic leads and tubing (both air and liquid supply lines) would be visible in this figure leading from movable arm 30 to appropriate fluid reservoirs or electronic control equipment. These lines are not shown in FIG. 1 for the sake of clarity but are described later with respect to specific parts of the apparatus. These supply lines are sufficiently long and flexible so as to allow ready access of movable arm 30 to any location within the operating space required to carry out the operations of the apparatus. The various supply lines are usually retained in the upper portion of the interior framework 20, typically by use of an elastic supporting yoke that is attached to the supply lines and to various locations on the framework 20.

Figure 2:
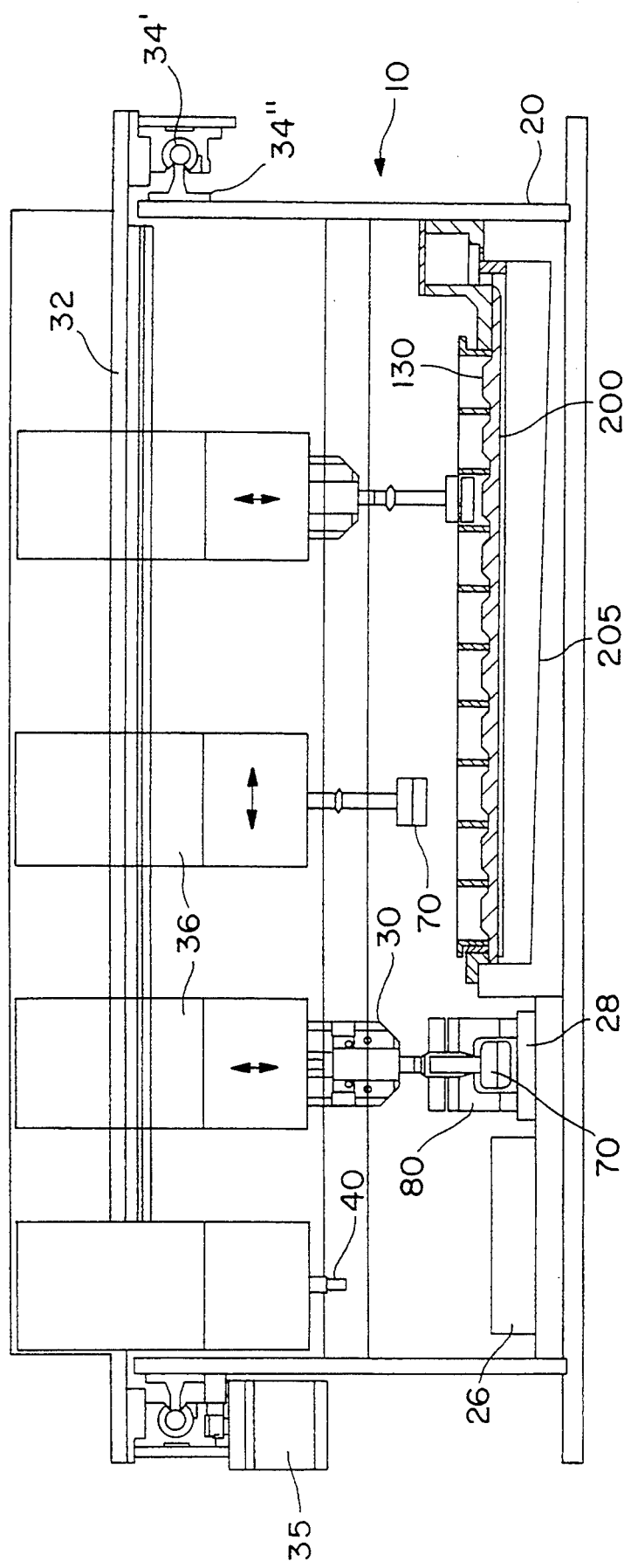
FIG. 2: Front view of the embodiment of FIG. 1 showing four separate locations and operational movements of the movable arm of the apparatus.

The same embodiment 10 of FIG. 1 is shown in FIG. 2. In this front view of the first embodiment of the invention, the movable arm 30 is shown in four different locations (i.e., FIG. 2 does not show four separate movable arms but merely four locations for a single arm). The left-most position of arm 30 is simply the home position to which the arm returns when not being used, which is selected for minimum interference with other operations, such as the insertion of microscope slides or disposable pipet tips into the cabinet-like interior of framework 20. The second position of arm 30 shown in FIG. 2 is at the location for pickup of removable wash/blow tip 70, which is retained in its wash/blow tip holder 80 at a fixed location on framework 20. The double-headed arrow on Z-track 36 indicates that movable arm 30 is moved downward at this location so that hollow tip head 40 is inserted into the stem of wash/blow head 70. Wash/blow tip holder 80 is adopted to surround and retain wash/blow tip 70 so that an upward motion of the arm while the tip is in its normal resting position will remove tip head 40 from tip 70. However, the front of wash/blow tip holder 80 is open so that a forward motion of arm 30 releases tip 70 from holder 80.

After wash/blow tip 70 is moved forward and released from its holder 80, movable arm 30 is moved upward so that tip 70 is above any interfering part of the apparatus, and wash/blow tip 70 is moved to an appropriate location while the tip is in the raised position as shown by the third position of the movable arm with a double-headed horizontal arrow on Z-track 36. When the movable arm reaches the appropriate location above a pre-selected microscope slide, as shown in the fourth position of the movable arm 30, the arm is again lowered to position the wash/blow tip at an appropriate height above the selected microscope slide. In a preferred embodiment, tip 70 is positioned at one end (e.g., the front end) of microscope slide 130 and a buffer or wash liquid supplied through liquid supply line 62 (not visible in this figure; see FIG. 12) as tip 70 is moved in a single pass to the rear of microscope slide 130. If desired, the blow-dry operation can then be carried out on the same slide by supplying pressurized air through an air supply line as tip 70 is moved back to the front position of microscope slide 130. However, it is also possible and preferred in some embodiments to move tip 70 to a second microscope slide for addition of buffer so that buffer added to the first microscope slide can remain on the slide for a pre-selected period of time prior to removal. After buffer has been added to a pre-selected number of slides, movable arm 30 is returned to the first slide of the group, and the blow operation can commence.

After completion of a wash cycle in the manner described, movable arm 30 is returned to the pickup position shown in the second location of the movable arm, and wash/blow tip 70 is removed from hollow tip head 40 by lowering arm 30 to the appropriate height in front of wash/blow tip holder 80, moving wash/blow tip 70 into holder 80, and raising arm 30 so that tip 70 is retained in holder 80. Movable arm 30 is then available for other operations as described below.

Holder 80 is adapted to closely retain tip 70 in a single ruled position. Although this can be accomplished in a variety of ways, FIGS. 1 and 2 illustrate an embodiment in which the neck of tip 70 (see FIG. 6 for detailed views of wash/blow tip 70) is closely retained in a press fit segment that forms the upper portion of holder 80. The press fit segment closely retains the stem of tip 70 and prevents it from being removed in an upward direction but allows removal in a forward direction. Thus, movable arm 30 can return to holder 80 and always find the stem of tip 70 available for pick up and further use.

Figure 3:
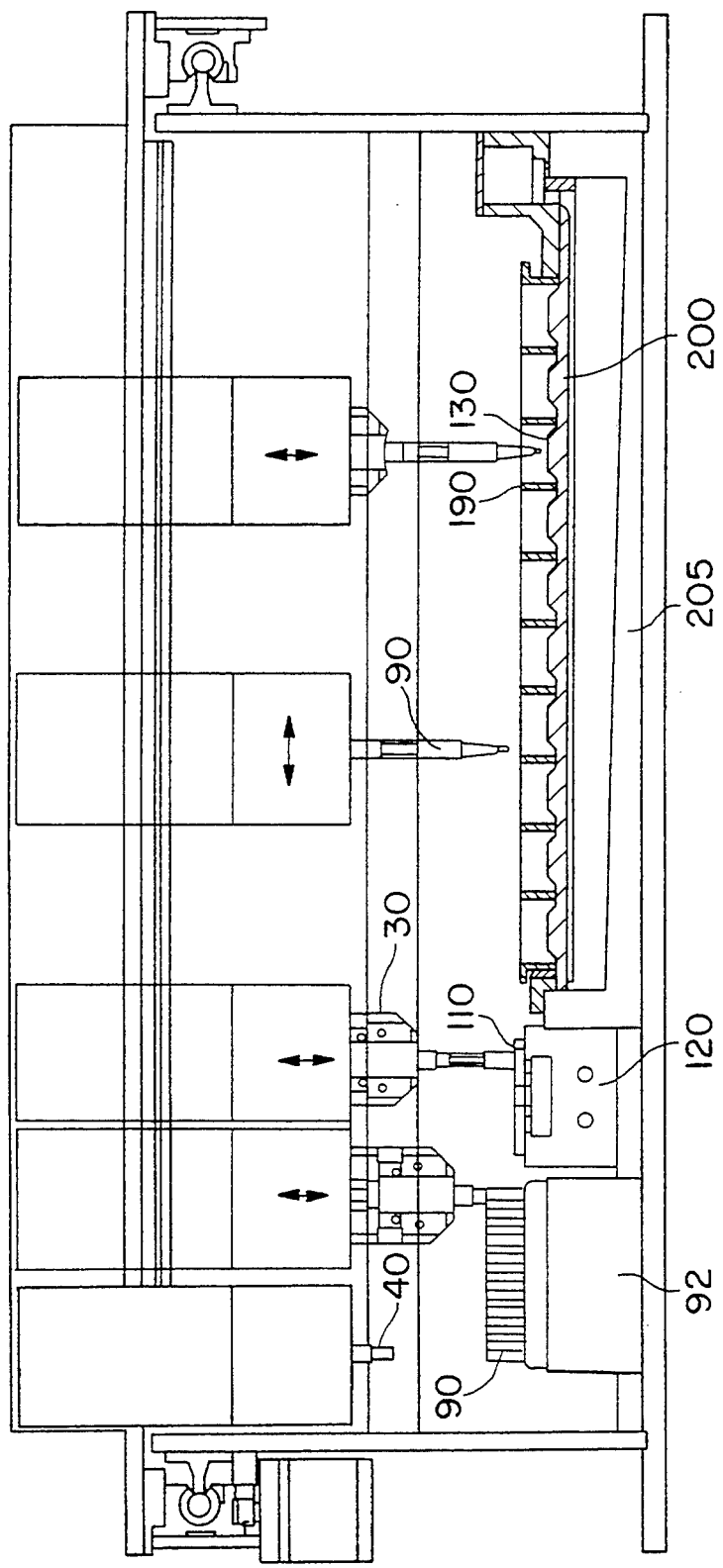
FIG. 3: Front view of the same embodiment shown in FIG. 2 showing additional operations with a second type of tip on the movable arm.

FIG. 3 is another front view of the same embodiment shown in FIGS. 1 and 2 in which again the movable arm is shown in multiple locations to show positioning of the single movable arm for different reagent-application operations. Again, as in FIG. 2, the left-most position is the home position of arm 30. The second position shows arm 30 moved to a location above a pipet tip 90 in a standard pipet tip box 92 that has been positioned onto base (reagent application tip holder) 100. Lowering movable arm 30 presses hollow tip head 40 into a reagent application tip 90 (here a disposable pipet tip) where the pipet tip is retained on hollow tip head 40 by a press fitting in the same manner in which tips are now used on hand-operated repeating pipets. Movable arm 30 is then raised and moved to the third arm position shown in FIG. 3, where the pipet tip is lowered into a reagent container 110 held in a fixed location by a reagent container holder 120. By supplying negative pressure through the pipet tip, reagent is withdrawn into the disposable pipet tip 90 for application to appropriate microscope slides. A measured volume of reagent is withdrawn by supplying negative air pressure to hollow tip 40 (i.e., withdrawing air through hollow tip 40). Although an apparatus of the invention can contain an element specifically designed with this operation, the embodiment shown in FIGS. 1–3 uses a standard liquid dispensing system and the liquid located in the supply line to act as a piston for withdrawing specific volume of air and thus drawing up specific volumes of reagents into reagent tip 90. This part of the apparatus is shown in more detail in FIG. 12. Reagent tip 90 is then raised as before and moved as shown in the fourth head position while raised to an appropriate location above a pre-selected microscope slide. At the pre-selected position, shown in the fifth position of movable arm 30, the reagent tip 90 is lowered, and reagent is applied to the slide again using the commercial liquid dispensing system showing in FIG. 12 and the liquid retained in the supply line to act as a piston. Reagent can be applied to a single microscope slide 130, or aliquots of the reagent in tip 90 can be applied to different microscope slides.

After the reagent is added to the last slide, movable arm 30 is returned to a position above drain bin 26, and a solenoid located on movable arm 30 releases reagent tip 90 into drain bin 26 for later removal. Operation of the solenoid is described in later Figures.

After removal of reagent application tip 90, hollow tip head 40 is again available for further operations.

Figure 4A:
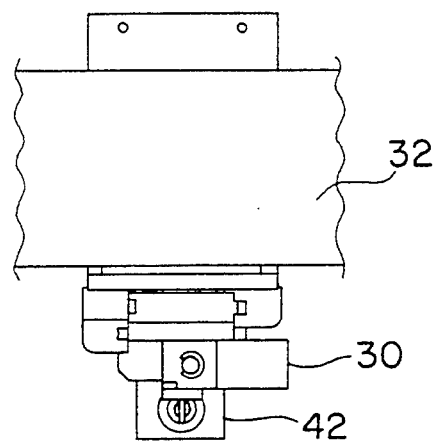
FIG. 4: Three views of the movable arm of the embodiment shown in FIGS. 1–3.
Figure 4B:
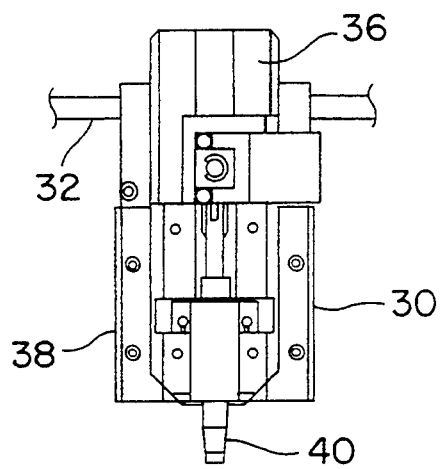
Figure 4C:
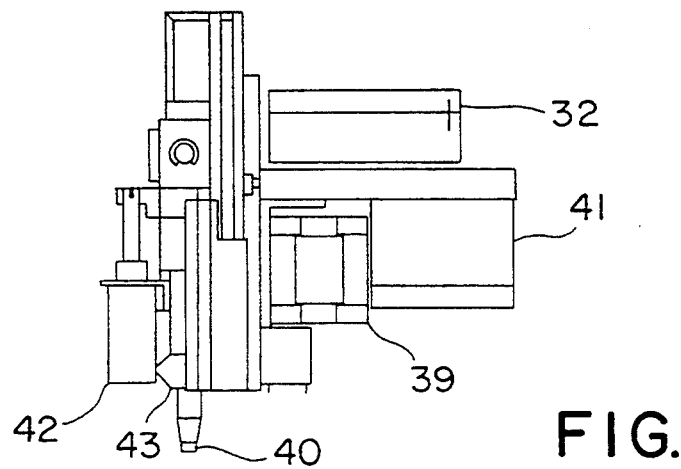

FIG. 4 is a series of three views of movable arm 30. In the plan view, some of arm 30 is obstructed by the X-axis track 32. However, a portion of arm 30 is visible at the bottom of the plan view, including solenoid 42 that is used for tip removal.

The front view of FIG. 4 shows Z-track 36 and Z-slide 38 which moves along track 36 under control of the Z-axis motor 39 which is visible in the side view of FIG. 4. The side view of FIG. 4 also shows X-axis motor 41, along with the X-track 32.

Operation of tip release solenoid 42 is most apparent from this side view of FIG. 4, as activation of the solenoid causes slide member 43 to be moved downward, thereby pressing a retained tip off the end of tip head 40. Slide 43 then returns to its normal position (as shown in this figure) so that another tip can be placed on tip head 40.

Figure 5C:
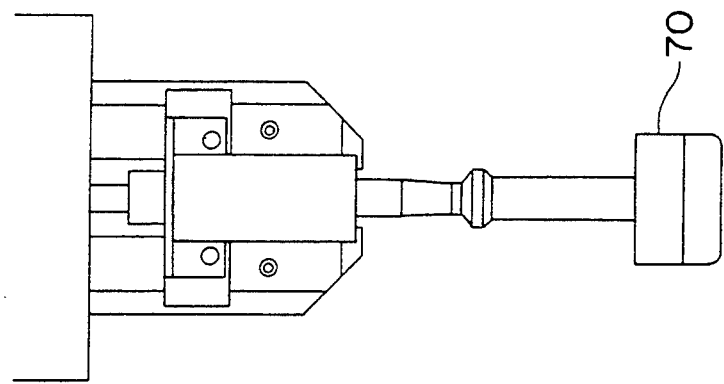
FIG. 5: Three front views of the movable arm shown in FIG. 4 in which the tip head is either empty or bears either of two tips used in the operation of the apparatus.
Figure 5B:
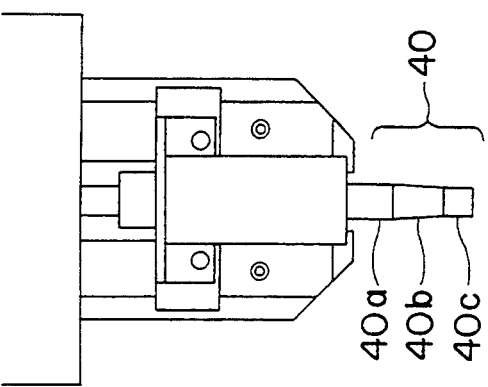
Figure 5A:
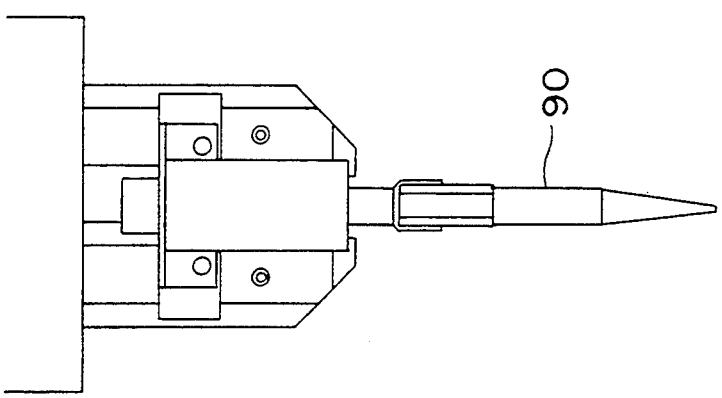

FIG. 5 shows three views of the movable arm 30, with the center view showing hollow tip head 40 without having a tip present on the head. In the embodiment shown, tip head 40 has three different diameters at different locations, namely a segment 40a that is sufficiently large to act as a stop when press-fitting a reagent tip 90 onto tip head 40, an intermediate section 40b that acts as the press-fit location for reagent application tip 90, and a smaller-diameter segment 40c at the end of tip head 40 that is sized to fit the wash/blow tip. Thus, as shown in the rightmost view of arm 30 in FIG. 5, hollow tip head 40 is inserted into wash/blow tip 70 only as far as segment 40c, while the left-most view of FIG. 5 shows hollow tip head 40 being inserted into a disposable pipet tip 90 as far as the dividing line between segment 40a and 40b. Thus, the reagent application tip 90 is removed when solenoid 42 moves as far down hollow tip head 40 as segment 40b, with the solenoid slide ring (not visible in this view) simply pushing pipet tip 90 off the end of hollow tip head 40. Solenoid 42 is not used to remove wash/blow head 70, since removing a reusable tip in this manner will not allow easy pickup. Instead, the reusable tip 70 is removed by inserting into a holder as previously described. In preferred embodiments of the invention, the solenoid release mechanism described above is generally used for disposable tips, while a press fitting and specifically designed holder are used for reusable tips so that such tips will be retained in the proper orientation for further use.

Figure 6A:
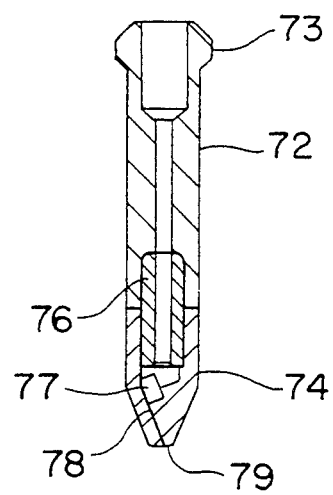
FIG. 6: Three detailed views of a wash/blow tip used in the embodiment of FIGS. 1–3.
Figure 6B:
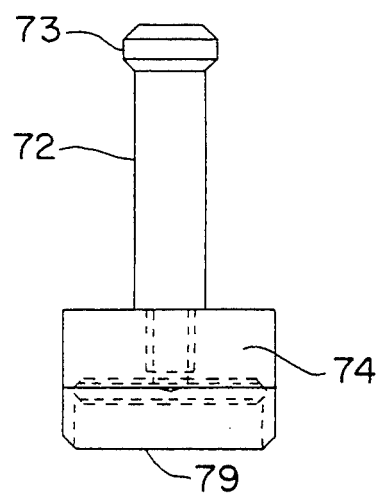
Figure 6C:
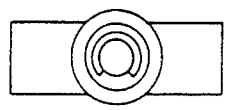
Figure 8A:
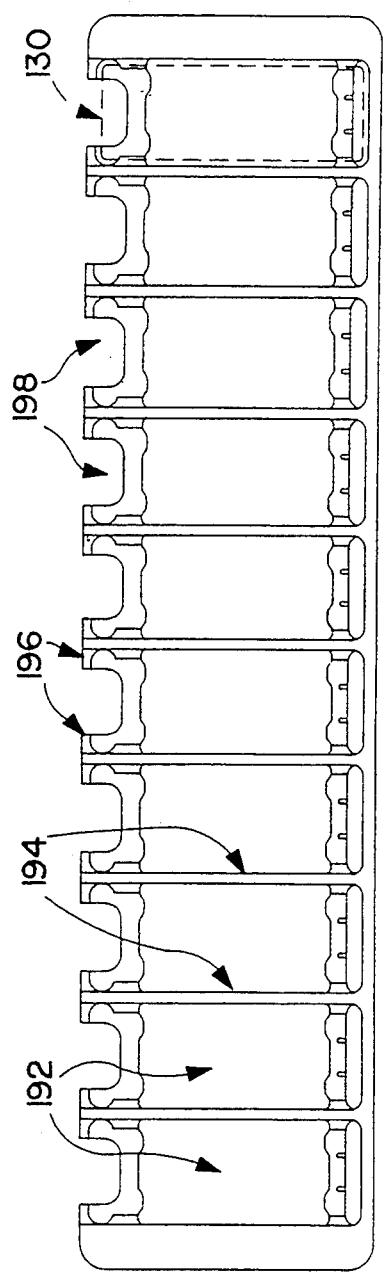
FIG. 8: Six views of an individual microscope slide tray used in the embodiment shown in FIGS. 1–3.
Figure 8B:
Figure 8C:
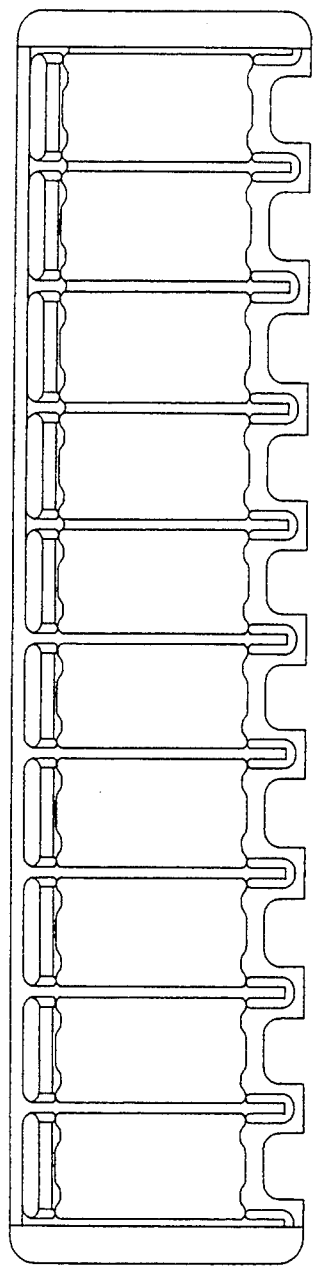
Figure 8D:
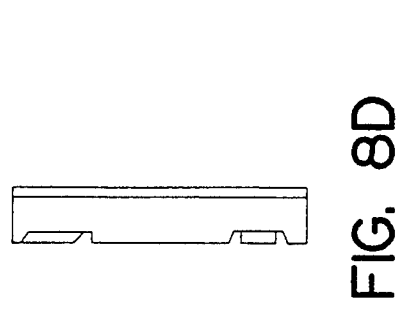
Figure 8E:
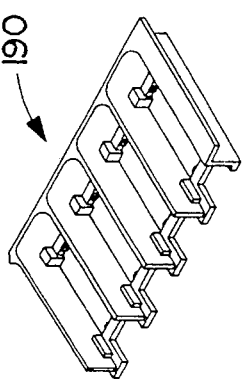
Figure 8F:
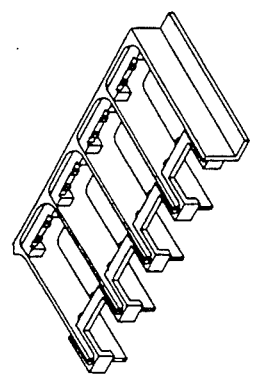

FIG. 6 shows a series of three detailed views of wash/blow tip 70. In the front view of FIG. 6, solid lines are used to indicate exterior surfaces and dashed fines are used to indicate interior surfaces.

In the sectional side view of FIG. 6, the hollow interior of tip head 40 is visible, as is the formation of tip head 40 from three parts. It is preferred to have the tip head formed from at least two parts, so that the interior hollow space will be available for cleaning. In the embodiment shown in FIG. 6, three pieces are present: a stem 72, a head 74, and a press-fit connector 76. Stem 72 is specifically adapted to be releasably held by holder 80 as previously described. A raised lip 73 is provided at the top of stem 72 which functions in combination with head 74 to act as top and bottom stops, respectively, when stem 72 is pressed into holder 80 as described above in the description of the operation of the wash/blow tip associated with FIG. 2.

The hollow interior of tip 70 is not limited to the specific shape shown, although certain advantages are obtained for aspects of this interior shape and slit shape as described below. In general, the hollow interior 77 of the head can vary significantly in shape as long as sufficient access is provided for easy flow of fluid into interior space 77 so that pressure differentials do not build up and cause differential exit of air or liquids through exit slot 79. Exit slot 79 is generally located on the bottom-most surface of tip 70 and is preferably a linear exit slit having a length substantially equal to the width of a standard microscope slide of the type selected for use at a given time. As there are different sizes of microscope slides, different wash/blow tips 70 can be prepared for each such microscope slide.

As shown in the sectional side view of FIG. 6, access 78 between hollow interior space 77 and exit slit 79 is preferably provided so that air leaving slit 79 exits at an angle to the vertical. By providing air exiting slit 79 at an angle and moving the head in a direction toward the obtuse angle formed between the air wall and the microscope slide, removal of water or buffer from the slide is enhanced.

FIG. 7 shows several typical reagent dispensing patterns on a microscope slide. Most slides have a specimen area 132 and an area for writing information on the slide 134. Because of the nature of the operation of mounting specimens on slides, a tissue sample can be present at any location in area 132. As previously discussed, the thin film of buffer that will be present when staining reagent is added to the slide assists in ensuring that adequate reagent is added to the tissue sample, regardless of where the sample is located or reagent is applied. However, in a preferred embodiment of the apparatus and method, the reagent is dispensed in a pattern rather than a single location so that a distance that a reagent must diffuse through the liquid film is reduced. Several typical reagent dispensing patterns are shown, although other patterns are equally viable.

Although many staining operations can be carried out without heating the slides, some staining techniques can be enhanced by providing heat so that either incubation or drying times are shortened, thereby increasing the speed of the overall operation. Numerous techniques exist for heating microscope slides and can be adapted to the present apparatus. A preferred embodiment involving such a heater in combination with a microscope slide holder involving a removable tray for multiple microscope slides is shown beginning in FIG. 8. This figure shows six views of a tray 190 intended to hold ten standard 1"×3" (2.5×7.5 cm) microscope slides. Tray 190 is formed into a series of individual wells 192 for microscope slides; the location of a single microscope slide 130 is shown by a dotted line in the right-most well of the plan view of FIG. 8. For reasons that will become apparent later, the bottom of the individual wells is open; this opening will allow the surface of a heating block to directly contact the bottom of each microscope slide. Individual side walls 194 separate each well 192 from its adjacent wells to prevent accidental contact of liquid (such as might occur during a washing operation). The open bottom of the wells 192 also allows buffer to drain through the bottom of tray 190 where it will be disposed off, typically in a drain pan shown in later figures. The side walls and retaining tabs 196 closely retain microscope slides placed into the individual wells. A gap 198 is present at one end of the well to allow easy grasping of an individual microscope slide between thumb and forefinger for insertion into and removal from tray 190.

Removable trays 190 are designed from ease of operation by allowing a user to place microscope slides in a loading tray outside the cabinet in which staining operations will occur. The tray also fits precisely into other elements at the appropriate location on base plate 22. However, other embodiments are possible, such as embodiments in which microscope slides are placed directly into permanent wells located inside the supporting framework of the apparatus.

Figure 9A:
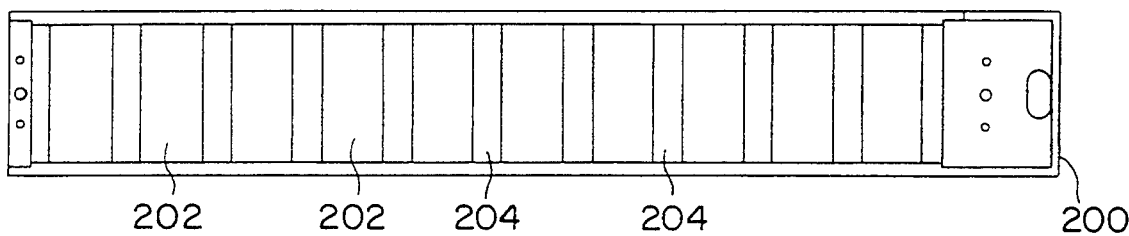
FIG. 9: Two views of a heater block element for use in the embodiment of FIGS. 1–3.
Figure 9B:
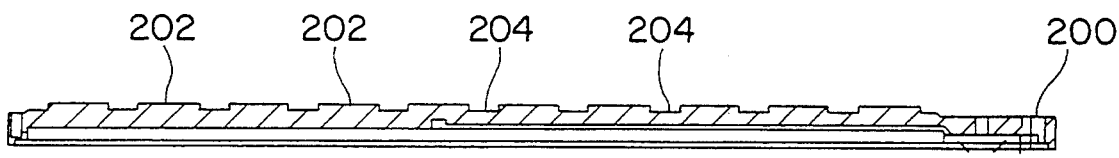

An individual heating block that will be used with the tray is used in FIG. 9. Two views are shown, namely a plan view, and a cross-sectional view. As seen most clearly in the cross-sectional view, the surface of the heating block 200 is divided into a number of raised areas 202 and depressions 204. Depressions 204 are sized to closely fit the bottom edges of slide carrier tray 190. When the bottom edges of tray 190 are placed in these depressions, raised areas 202 press upward into the open bottoms of the wells of the tray and closely contact the individual microscope slides while also acting to precisely locate tray 190 relative to the location of heating block 200.

Figure 10:
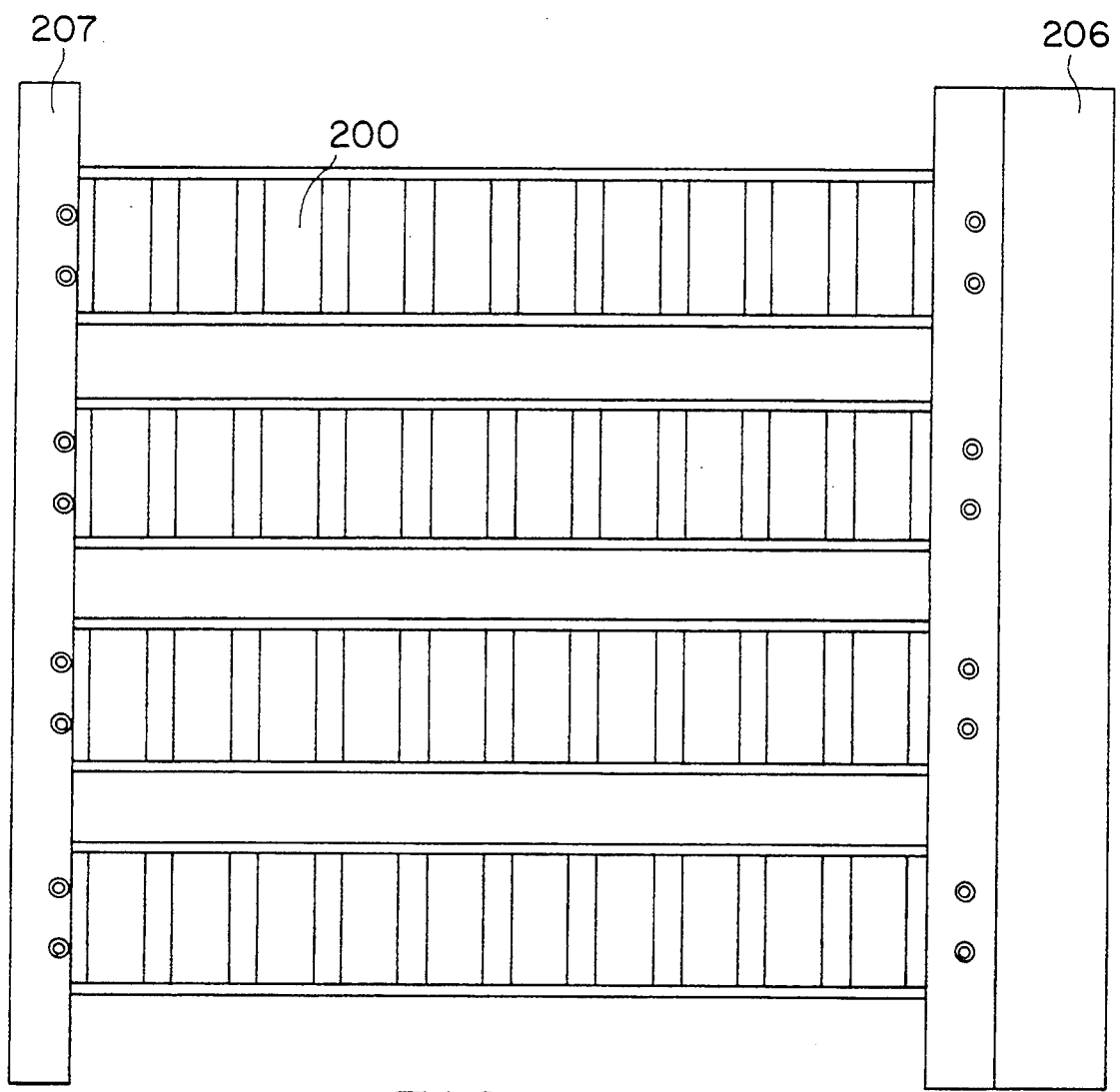
FIG. 10: Plan view of a heater block assembly for use in the embodiment of FIGS. 1–3.

Each of the individual heater blocks 200 shown in FIG. 9 can be assembled into an array of multiple blocks as shown in FIG. 10 using mounting blocks 206 and 207. It is then possible to individually heat each of the heater blocks to different temperatures, thereby concurrently providing different temperatures of operation for different reagent configurations without operator intervention. In the embodiment shown in FIG. 1, each of the individual heater blocks is heated electrically for easy temperature control.

The heater block assemblies can be mounted on a drain pan for ready disposal of wash fluid. FIG. 11 shows plan and front sectional views of the heater block assembly shown in FIG. 10 mounted on a drain pan 205 and bearing four microscope slide trays 190, each of which is capable of containing 10 slides for a total of 40 microscope slides in a fixed array. The sides of the microscope slide tray 190 prevent contamination between adjacent microscope slides, and the open bottom of tray 190 and the space between individual heater blocks 200 allow ready draining of wash fluid from the individual microscope slides.

Figure 12:
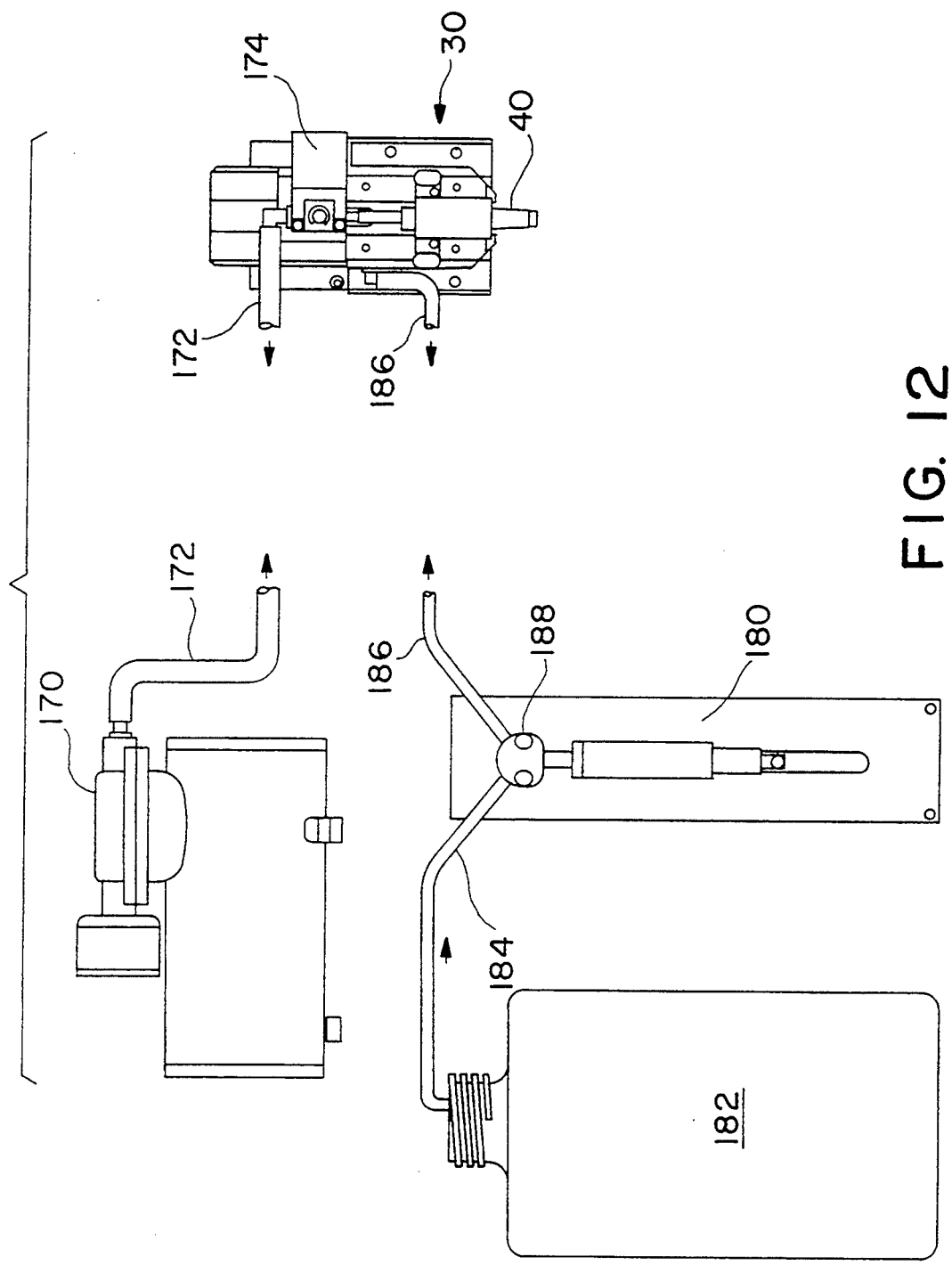
FIG. 12: Three details showing parts of the apparatus that supply air and wash fluid to the dispensing arm along with an indication of the attachment of the supply lines and the switches present on the movable arm.

FIG. 12 shows three views of various components used in the supply of air and wash liquid to head 30. Although air can be supplied by a compressed air container and regulator, in the embodiment shown in FIG. 1 a compressor 170 (and surge reservoir) provides air through flexible line 172 to movable arm 130 and ultimately to hollow tip 40. An air shut-off valve 174 is located in this line and is controlled by control means 150 (not visible in this figure). Buffer or other wash solution is supplied by a component that allows delivery of measured volumes of liquid, such as a commercially available, electrically operated automatic dispensing pipet 180. Buffer in a reservoir 182 is supplied by supply line 184 to diluter 180 and hence through supply line 186 to movable head 30 and ultimately hollow tip 40. Diluter 180 in the embodiment shown acts as a shut-off valve, so that no further valving is required. Additionally, the liquid present in line 186 is essentially inelastic and acts as a piston for withdrawing or dispensing measured volumes of air through hollow tip 40. For example, during a washing operation as described above, both line 186 and hollow tip 40 on movable head 30 are filled with wash liquid. During the blow operation, air is released by shut-off valve 174 and blows buffer out of hollow tip 40. However, since diluter 180 is shut-off at this time, liquid can not be forced back into diluter 180 through line 186 but is retained in line 186. After the completion of a blow operation and pick up of a reagent dispensing tip 90 onto hollow tip head 40, the next operation will be withdrawal of reagent from a reagent container into pipet tip 90. Thus, even if the amount of liquid retained in line 186 is slightly variable, the next operation is withdrawing of liquid further into line 186 by a precise amount under the control of controller 150 and diluter 180, so that the actual amount of liquid present in supply line 186 makes no difference in the measurement operation. Likewise, in the dispensing of the aliquots of reagent on individual slides, wash liquids will not be expelled from line 186, since no more liquid will be returned to line 186 by diluter 180 than was originally withdrawn. Thus, diluter 180 and the liquid present in line 186 operate to supply the desired negative and positive air pressure for dispensing reagent to the individual slides.

As will be apparent from the operation as described above, a valve 188 is present as part of diluter 180 so that the diluter withdraws and dispenses liquid through the appropriate line 184 or 186 for different operations.

It will be apparent to one of ordinary skill that many of the specific elements shown in the figures and described above can be replaced by other elements that perform the same function. For example, the XYZ tracks can be replaced by a single robotic arm. Additionally, it will be understood that the specific tracks, motors, and other individual parts can be replaced by other parts of equivalent function. In a preferred embodiment of the invention, the XYZ tracks were purchased as commercially available sliding tracks. The X-axis and Z-axis motions are supplied by a linear motion raft and linear motion guide (Part No. SR20W from THK) and a stepping motor (Part No. 4023-819 for the X-axis and 5017-009 for the Z-axis, both supplied by Applied Motion). The two mils of the Y-axis shaft system are a linear bearing raft assembly (Part No. SRA-8-XS) and linear bearing pillow block (Part No. SPB-8-OPN-XS), both supplied by Thomson; power along the Y-axis was supplied by the same stepping motor used for the X-axis. Other commercially available components used in the embodiment shown in FIGS. 1–3 include a Thomas Industries, Inc. Model No. 107CA18 compressor, a Cavro XL-3000 automatic diluter and a NAC Valves, Inc., Model No. 35A-AAA-0AAA-IBA air shut-off valve. Electrical connections, tubing, compressed air distribution systems, liquid distribution systems from a central reservoir, and many other components such as holders for a standard pipet tip box or for reagent containers are commercially available from a variety of suppliers. Thus, the apparatus of the invention can be prepared from readily available commercial parts assembled in the manner described, with a minimum number of specific manufacturing techniques. Since the blow-dry head (70 in the figures) is not readily available, it will typically be manufactured for a particular apparatus as shown or in a similar manner to provide the features that are described in the specification above.

The composition of the components from which various parts are manufactured can vary widely, but components through which reagents pass or which contact potentially corrosive reagent or wash solutions are typically prepared from stainless steel or inert plastics to prevent corrosion. The wash/blow head is typically formed from a moldable plastic (such as a polyacrylate) and can be prepared by a molding process, a plastic-shaping process, or some combination thereof depending on the individual shape chosen by a user. Parts that are subject to wear, such as the stem of the wash/blow head 70 and hollow tip head 40 are typically prepared from a hard plastic or other material that will resist wear.

The apparatus is typically operated under the control of a computer or other programmable control device. In the simplest applications where only a single type of automated staining will be done repeatedly, it is possible to provide either a hard-wired controller or a non-programmable electronic controller, such as a computer operating under instructions from read-only memory. In preferred embodiments, however, a programmable controller or computer is used so that the operation can be varied. Software will generally be provided with the computer so that the user does not need to provide instructions for individual motions, but merely selects appropriate motions from a menu. In a typical operation, a user would be asked to select the location and volume of the reagents, the location of the slides being treated, and the length of time of various steps such as incubation times (and if necessary the temperature); all other operations will be carried out by the pre-programmed instruction set in the memory of the computer, which will control actual movement of the movable arm to the appropriate locations and activation of the various air and liquid control systems.

A key step in the method that is used in the automated apparatus of the invention involves blowing excess reagent or buffer off the surface of the slide. A preferred embodiment of the tip used in this blowing operation is shown in FIG. 6, although other tips having slits for exit of air to provide a wall of air can also be used. By adjusting the air pressure, height of the exit slit above the microscope slide, and rate of movement of the slit, the extent to which liquid is removed from the slide can be varied. The mount of liquid present in the thin film on the microscope slides upper surface is quite small, typically being from 2 to 25 microliters, more generally from 3 to 20, and preferably from 5 to 10. The area of concern is approximately 15 cm$^2$, providing a typical volume per surface area of 0.13 to 1.7 microliter/cm$^2$. However, it is difficult to determine the actual volume being used, since the operation of blowing liquid off the top surface of a slide causes liquid to adhere to other portions of the microscope slide, making measurement of the remaining liquid difficult. Thus, the volume of liquid present on the slide upper surface at the end of a blow-dry operation is best determined empirically. The maximum permissible volume is determined by the stain being used and its concentration at the reagent application stage, since these factors affect the final concentration of the stain or other reagent on the surface of this slide. Historical procedures developed for slide preparation are generally described in terms of a particular reagent concentration, incubation time, and temperature. Accordingly, it is desirable to provide a minimum volume of liquid on the slide in order to avoid having to change the concentration of reagents from the standard used in the industry. By adhering to this guideline, it is possible to use commercially available, already prepared stain solutions as reagents.

On the other hand, too little liquid on a slide can cause problems in reagent spreading, particularly because of evaporation. Since buffer is added to a slide prior to addition of reagent and motion of the moveable arm to pick up reagent application tips and reagents takes time, the buffer must remain on the slide until reagent is added, which further may not occur until after preparation of other slides. Since it is more efficient to prepare multiple slides at one time rather than to require repeated movements of the movable arm and repeated pickup motions for the various heads, a typical minimum volume of buffer would be that amount which is sufficient to allow preparation of at least four slides without requiring removal of a given tip.

The air pressure, height of the head above the slide, and rate of motion of the head for control of the liquid film can all be selected by the user or by the manufacturer of the apparatus. Generally, the same air pressure will be used at all time so as to remove this variable from consideration. Thus, only the height of the head and the rate of motion will typically be varied. The higher the height of the head above the slide, the less liquid is removed. The faster the head is passed across the slide for a given height, the less liquid is removed.

For a standard 1 inch by 3 inch (2.5×7.5 cm) microscope slide surface area and a wash/blow tip having the configuration shown in FIG. 6, an air pressure of 7 psi (0.5 atm.), a height of 0.07 inch (2 mm) above the microscope slide surface, and a rate of motion of 3 inch/sec (7.5 cm/sec) provide a preferred buffer film suitable for the staining of 4 slides at 25° C. and a relative humidity of 60–80%, which is the typical humidity present inside a closed and operating apparatus of the invention.

The wash solutions used in the apparatus of the invention can vary significantly depending on the staining technique being used. A typical wash solution is an aqueous solution of a surfactant and can contain other components present in typical slide preparation of wash solutions, such as buffers. In preferred embodiments, sufficient surfactant is present to provide a surface tension in a solution equivalent to that present in solutions containing water in the following surfactants at the concentrations listed. Typical surfactants used (with concentrations shown in parenthesis) are TWEEN 20 (0.02 to 2% v/v), BRIT 35 (0.05 to 2% v/v), and TRITON X-100 (0.01 to 1% v/v). Typical buffers used (with pH shown in parenthesis) are phosphate buffered saline (7.6) and TRIS-CL (7.6). For conciseness of language, the specification and claims often referred to water as the wash fluid or the fluid being removed at a particular step. It will be apparent that this "water" can and generally is an aqueous solution of buffer and surfactant or of some staining reagent.

It will be apparent that the apparatus and method of the invention can be used in any staining technique that can be carded out manually and that there are no limitations placed on the invention by the staining technique.

The apparatus of the invention can contain a number of further components designed for ease of operation. For example, drain trays with exit lines to waste reservoirs can be located either individually under components of the apparatus or a single drain tray and collection system can be provided for the entire interior space of the apparatus frame. In a typical apparatus, the frame is a form of a cabinet with an interior space in which all operations take place. A closable access port (e.g., door) is provided to allow an operator to add the various removable components to the interior cabinet space. A transparent door can be provided to prevent accidental spraying of liquid (as during a drying operation) into the room in which the apparatus is located while allowing the operator of the apparatus to visually verify correct operation. Other optional features that can be included on the apparatus include devices intended to ensure level operation, to protect against electric shock, to verify that an appropriate tip has been selected and properly placed on the tip head, or to optically scan slides in a microscope slide tray or other container for microscope slides so that a human operator does not even need to enter information into the computer. Such information could be provided, for example, by a standard bar code attached to an individual microscope slide or other component. Multiple reagent containers can be provided so that different staining operations can be carded out under control of the bar code and the computer and its pre-program software.

All publications and patent applications mentioned in this specification are herein incorporated by reference to the same extent as if each individual publication or patent application was specifically and individually indicated to be incorporated by reference.

The invention now being fully described, it will be apparent to one of ordinary skill in the art that many changes and modifications can be made thereto without departing from the spirit or scope of the appended claims.

What is claimed:

1. An automatic apparatus for staining a microscope slide, comprising:
 a supporting framework;
 an arm moveable in three dimensions attached to said framework;
 means for moving said arm;

a hollow tip head located on said arm;

means for alternatively supplying positive or negative gas pressure to said hollow tip head to withdraw or dispense gas or liquid through said hollow tip head;

a removable wash/blow tip having an exit slit substantially equal in length to the width of said microscope slide, said wash/blow tip being adapted to be removably attached to said hollow tip head by a preselected movement of said arm;

a wash/blow tip holder at a first fixed location on said framework;

a reagent application tip holder at a second fixed location on said framework for holding a reagent application tip, said reagent application tip being adapted to be removably attached to said hollow tip head by a preselected movement of said arm;

a reagent container holder at a third fixed location on said framework;

a microscope slide holder at a fourth fixed location on said framework, said microscope slide holder being adapted to removably contain said microscope slide; and;

control means operatively connected to said means for moving said arm and said means for alternatively supplying positive or negative gas pressure, for controlling movement of said arm between said locations, to cause said tip head to pick up said wash/blow tip or said reagent application tip and to move to one or more of said locations to withdraw a reagent from said reagent container or to dispense said reagent on said slide through said reagent application tip or to dispense a gas or liquid over said slide through said wash/blow tip.

2. The apparatus of claim 1, wherein said supporting framework comprises a cabinet having an interior space and all of said locations are in said interior space.

3. The apparatus of claim 2, wherein said cabinet has a closeable access port.

4. The apparatus of claim 1, wherein said arm moves along independent X, Y, and Z tracks for independent movement of said tip head in three orthogonal directions.

5. The apparatus of claim 1, wherein said arm remains in a fixed location in the absence of power being supplied to said means for moving said arm.

6. The apparatus of claim 4, wherein said X and Y tracks are oriented in the horizontal plane of said apparatus when said apparatus is in its normal operating orientation.

7. The apparatus of claim 1, wherein said apparatus further comprises a liquid reservoir in selectable fluid communication with said hollow tip head.

8. The apparatus of claim 1, wherein said means for supplying gas pressure comprises a pressurized gas reservoir or compressor.

9. The apparatus of claim 1, wherein said means for supplying gas pressure is capable of withdrawing or dispensing a fixed amount of gas through said tip head, said fixed amount being selectable by said control means, thereby providing measured withdrawing or dispensing of a liquid into or from a reagent application tip attached to said hollow tip head.

10. The apparatus of claim 9, wherein said means for supplying gas pressure comprises a moveable piston that controls liquid in a liquid supply line between a liquid reservoir and said hollow tip head.

11. The apparatus of claim 10, wherein said means for supplying gas pressure comprises a pressurized gas reservoir or compressor, said moveable piston, and means for alternatively selecting said reservoir or said piston for dispensing or withdrawing of gas through said tip head.

12. The apparatus of claim 1, wherein said wash/blow tip attaches to said hollow tip head via a press fitting.

13. The apparatus of claim 12, wherein said wash/blow tip holder is adapted to release said wash/blow tip from said holder when said tip head is pressed by said arm onto said wash/blow tip and said tip head is withdrawn from said holder in a first direction relative to said holder.

14. The apparatus of claim 12, wherein said wash/blow tip holder is adapted to remove said wash/blow tip from said tip head when said wash/blow tip on said tip head is inserted into said wash/blow tip holder and said tip head is withdrawn from said holder in a second direction relative to said holder.

15. The apparatus of claim 1, wherein said reagent application tip holder is adapted to retain a container of disposable tips, whereby said tips are retained by said container as an array of tips at a fixed orientation for access by said tip head.

16. The apparatus of claim 1, wherein further comprising one or more additional holders for reagent containers at fixed locations on said framework.

17. The apparatus of claim 1, wherein said apparatus further comprises a heater for microscope slides at said fourth location.

18. The apparatus of claim 1, wherein said apparatus further comprises a removable microscope tray adapted to retain multiple microscope slides in a fixed array at said fourth location.

19. The apparatus of claim 18, wherein said tray comprises individual wells for microscope slides and said wells are partially open on their bottom surfaces.

20. The apparatus of claim 19, further comprising a microscope slide heating surface, wherein when said tray with any microscope slides contained in said tray is inserted into said microscope slide holder, said microscope slides contact said heating surface through the partially open bottom surface of said wells.

21. The apparatus of claim 20, wherein individual segments of said heating surface are controlled by said control means, thereby providing different temperatures for said segments.

22. The apparatus of claim 1, wherein said control means comprises a programmable computer.

23. The apparatus of claim 1, wherein said control means causes a gas to be blown through said wash/blow tip as said wash/blow tip is moved horizontally over said microscope slide.

24. The apparatus of claim 1, wherein said control means causes a reagent tip on said tip head to withdraw and hold for transfer a fixed volume of said reagent from said container, then causes said tip head to move to a location above a microscope slide in said microscope slide holder, and then causes said reagent tip to dispense a fixed volume of said reagent on said microscope slide.

* * * * *